United States Patent
Chou et al.

(10) Patent No.: US 12,070,323 B2
(45) Date of Patent: Aug. 27, 2024

(54) SYSTEM AND METHOD FOR GENERATING DIAGNOSTIC HEALTH INFORMATION USING DEEP LEARNING AND SOUND UNDERSTANDING

(71) Applicant: Google LLC, Mountain View, CA (US)

(72) Inventors: Katherine Chou, Palo Alto, CA (US); Michael Dwight Howell, Palo Alto, CA (US); Kasumi Widner, San Carlos, CA (US); Ryan Rifkin, Oakland, CA (US); Henry George Wei, Larchmont, NY (US); Daniel Ellis, New York, NY (US); Alvin Rajkomar, Mountain View, CA (US); Aren Jansen, Palo Alto, CA (US); David Michael Parish, Buffalo, NY (US); Michael Philip Brenner, Somerville, MA (US)

(73) Assignee: GOOGLE LLC, Mountain View, CA (US)

( * ) Notice: Subject to any disclaimer, the term of this patent is extended or adjusted under 35 U.S.C. 154(b) by 995 days.

(21) Appl. No.: 17/045,318

(22) PCT Filed: May 4, 2018

(86) PCT No.: PCT/US2018/031064
§ 371 (c)(1),
(2) Date: Oct. 5, 2020

(87) PCT Pub. No.: WO2019/194843
PCT Pub. Date: Oct. 10, 2019

(65) Prior Publication Data
US 2021/0361227 A1 Nov. 25, 2021

Related U.S. Application Data

(60) Provisional application No. 62/653,238, filed on Apr. 5, 2018.

(51) Int. Cl.
*A61B 5/00* (2006.01)
*G06N 20/00* (2019.01)
(Continued)

(52) U.S. Cl.
CPC .......... *A61B 5/4803* (2013.01); *A61B 5/7264* (2013.01); *A61B 5/7275* (2013.01);
(Continued)

(58) Field of Classification Search
CPC ... A61B 5/4803; A61B 5/7264; A61B 5/7275; G06N 20/00; G10L 25/63; G10L 25/66
See application file for complete search history.

(56) References Cited

U.S. PATENT DOCUMENTS 7,529,670 B1 * 5/2009 Michaelis .............. A61B 5/091
704/275
10,098,569 B2 * 10/2018 Abeyratne ............. G16H 50/30
(Continued)

FOREIGN PATENT DOCUMENTS

| EP | 1531457 | 5/2005 |
| EP | 3200188 | 8/2017 |
| WO | WO 2010123483 | 10/2010 |

OTHER PUBLICATIONS

Search Report for PCT/US2018/031064, mailed on Dec. 10, 2018, 3 pages.

*Primary Examiner* — Shirley X Jian
(74) *Attorney, Agent, or Firm* — DORITY & MANNING P.A.

(57) ABSTRACT

The present disclosure provides systems and methods that generating health diagnostic information from an audio recording. A computing system can include a machine-learned health model comprising that includes a sound model trained to receive data descriptive of a patient audio recording and output sound description data. The computing
(Continued)

system can include a diagnostic model trained to receive the sound description data and output a diagnostic score. The computing system can include at least one tangible, non-transitory computer-readable medium that stores instructions that, when executed, cause the processor to perform operations. The operations can include obtaining the patient audio recording; inputting data descriptive of the patient audio recording into the sound model; receiving, as an output of the sound model, the sound description data; inputting the sound description data into the diagnostic model; and receiving, as an output of the diagnostic model, the diagnostic score.

15 Claims, 7 Drawing Sheets

(51) Int. Cl.
  *G10L 25/63* (2013.01)
  *G10L 25/66* (2013.01)
(52) U.S. Cl.
  CPC .............. *G06N 20/00* (2019.01); *G10L 25/63* (2013.01); *G10L 25/66* (2013.01)

(56) References Cited

U.S. PATENT DOCUMENTS

| | | | |
|---|---|---|---|
| 10,896,763 B2* | 1/2021 | Kempanna | G06N 20/00 |
| 11,031,017 B2* | 6/2021 | Wang | G10L 15/04 |
| 11,442,614 B2* | 9/2022 | Strader | G06F 3/0482 |
| 11,688,404 B2* | 6/2023 | Wang | G10L 17/00 |
| | | | 704/232 |
| 11,763,188 B2* | 9/2023 | Watson | G06N 3/045 |
| | | | 706/12 |
| 11,864,880 B2* | 1/2024 | Abeyratne | A61B 5/0803 |
| 2009/0312660 A1* | 12/2009 | Guarino | G16H 50/80 |
| | | | 600/529 |
| 2015/0340034 A1 | 11/2015 | Schalkwyk et al. | |
| 2015/0380009 A1* | 12/2015 | Chang | G10L 21/00 |
| | | | 704/263 |
| 2017/0258390 A1* | 9/2017 | Howard | A61B 5/369 |
| 2018/0286430 A1* | 10/2018 | Shapira | A61B 5/7282 |
| 2018/0289308 A1* | 10/2018 | Lever | A61B 5/4803 |
| 2019/0340541 A1* | 11/2019 | Watson | G06N 20/00 |
| 2021/0202090 A1* | 7/2021 | O'Donovan | G16H 40/67 |

* cited by examiner

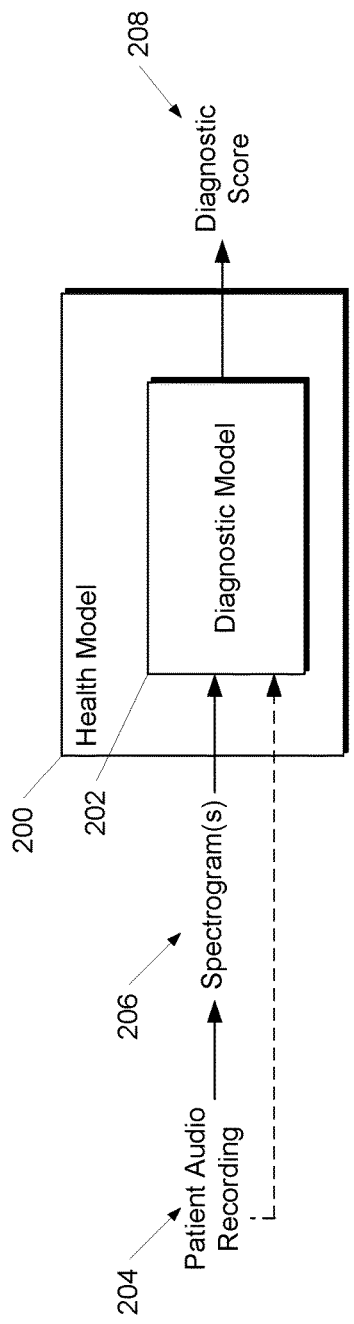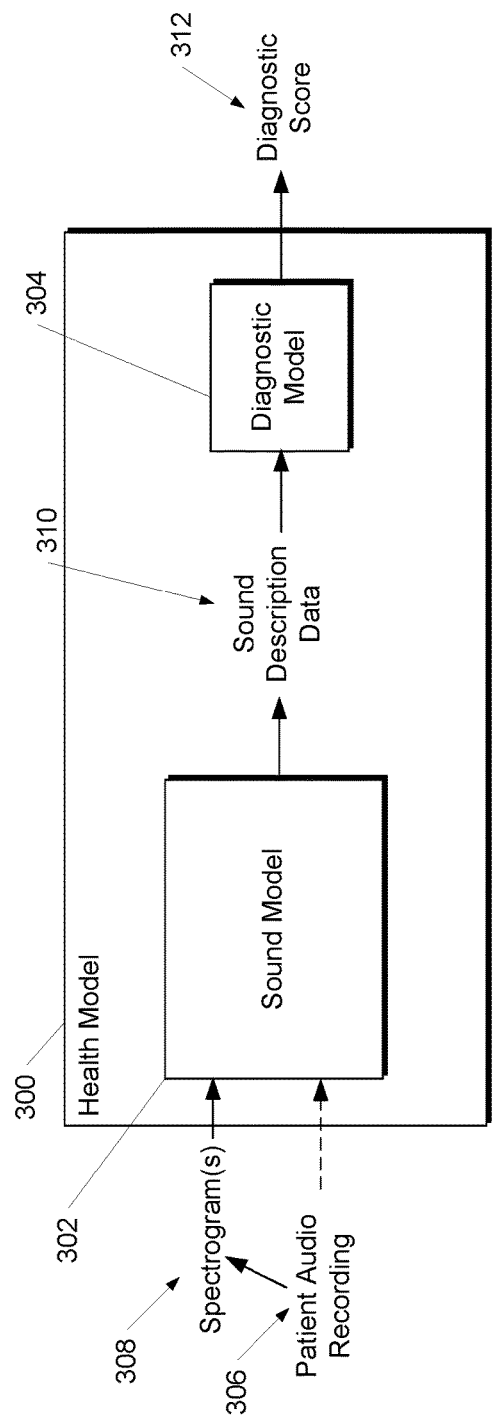

SYSTEM AND METHOD FOR GENERATING DIAGNOSTIC HEALTH INFORMATION USING DEEP LEARNING AND SOUND UNDERSTANDING

PRIORITY CLAIM

This application is based upon and claims the right of priority under 35 U.S.C. § 371 to International Application No. PCT/US2018/031064 filed on May 4, 2018, which claims the benefit of U.S. Provisional Application Ser. No. 62/653,238 filed Apr. 5, 2018. Applicant claims priority to and the benefit of each of such applications and incorporates all such applications herein by reference in their entirety.

FIELD

The present disclosure relates generally to machine learning. More particularly, the present disclosure relates to generating health diagnostic information from an audio recording or other audio data.

BACKGROUND

Currently, medical evaluations or consultations with doctors, nurses, or other qualified medical personnel are generally required to receive diagnostic information about potential health issues. In person consultations, however, can be time consuming, expensive, or inconvenient. Recently, telemedicine (e.g., consultations through video conferencing) has become more prevalent. While this provides improved access to medical professionals, telemedicine still requires the time and attention of a qualified medical expert.

Additionally, many health disorders can manifest symptoms that are subtle or otherwise difficult for both lay persons as well as professional health care providers to detect or accurately quantify. For example, some health disorders may cause minor variations in the patient's speaking ability or style. Others can affect sonic characteristics of coughs and sneezes.

SUMMARY

Aspects and advantages of embodiments of the present disclosure will be set forth in part in the following description, or can be learned from the description, or can be learned through practice of the embodiments.

One example aspect of the present disclosure is directed to a computing system. The computing system can include at least one processor and a machine-learned health model. The machine-learned health model can include a sound model and a diagnostic model. The sound model can be trained to receive data descriptive of a patient audio recording and, in response to receipt of the patient audio recording, output sound description data. The diagnostic model can be trained to receive the sound description data, and in response to receipt of the sound description data, output a diagnostic score. The computing system can include at least one tangible, non-transitory computer-readable medium that stores instructions that, when executed by the at least one processor, cause the at least one processor to perform operations. The operation can include obtaining the patient audio recording and inputting data descriptive of the patient audio recording into the sound model. The operations can include receiving, as an output of the sound model, the sound description data and inputting the sound description data into the diagnostic model. The operations can include receiving, as an output of the diagnostic model, the diagnostic score.

Another example aspect of the present disclosure is directed to a computer-implemented method including obtaining, by one or more computing devices, a machine-learned health model that comprises a sound model and a diagnostic model. The sound model can be trained to receive data descriptive of a patient audio recording and, in response to receipt of the data descriptive of the patient audio recording, output sound description data. The diagnostic model can be trained to receive the sound description data, and in response to receipt of the sound description data, output a diagnostic score. The computer-implemented method can include inputting, by the one or more computing devices, data descriptive of the patient audio recording into the sound model. The computer-implemented method can include receiving, by the one or more computing devices, as an output of the sound model, the sound description data. The computer-implemented method can include inputting, by the one or more computing devices, the sound description data into the diagnostic model. The computer-implemented method can include receiving, by the one or more computing devices, the diagnostic score as an output of the diagnostic model.

One example aspect of the present disclosure is directed to a computing system. The computing system can include at least one processor and a machine-learned health model. machine-learned health model can include a diagnostic model that is trained to receive feature data that describes a patient audio recording, and in response to receipt of the feature data that describes the patient audio recording, output a diagnostic score. The computing system can include at least one tangible, non-transitory computer-readable medium that stores instructions that, when executed by the at least one processor, causes the at least one processor to perform operations. The operations can include obtaining the patient audio recording and generating the feature data that describes the patient audio recording. The operations can include inputting the feature data that describes the patient audio recording into the diagnostic model and receiving, as an output of the diagnostic model, the diagnostic score.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which:

FIG. 2 depicts a block diagram of an example health model according to example embodiments of the present disclosure.

FIG. 3 depicts a block diagram of an example health model according to example embodiments of the present disclosure.

Figure 1A:
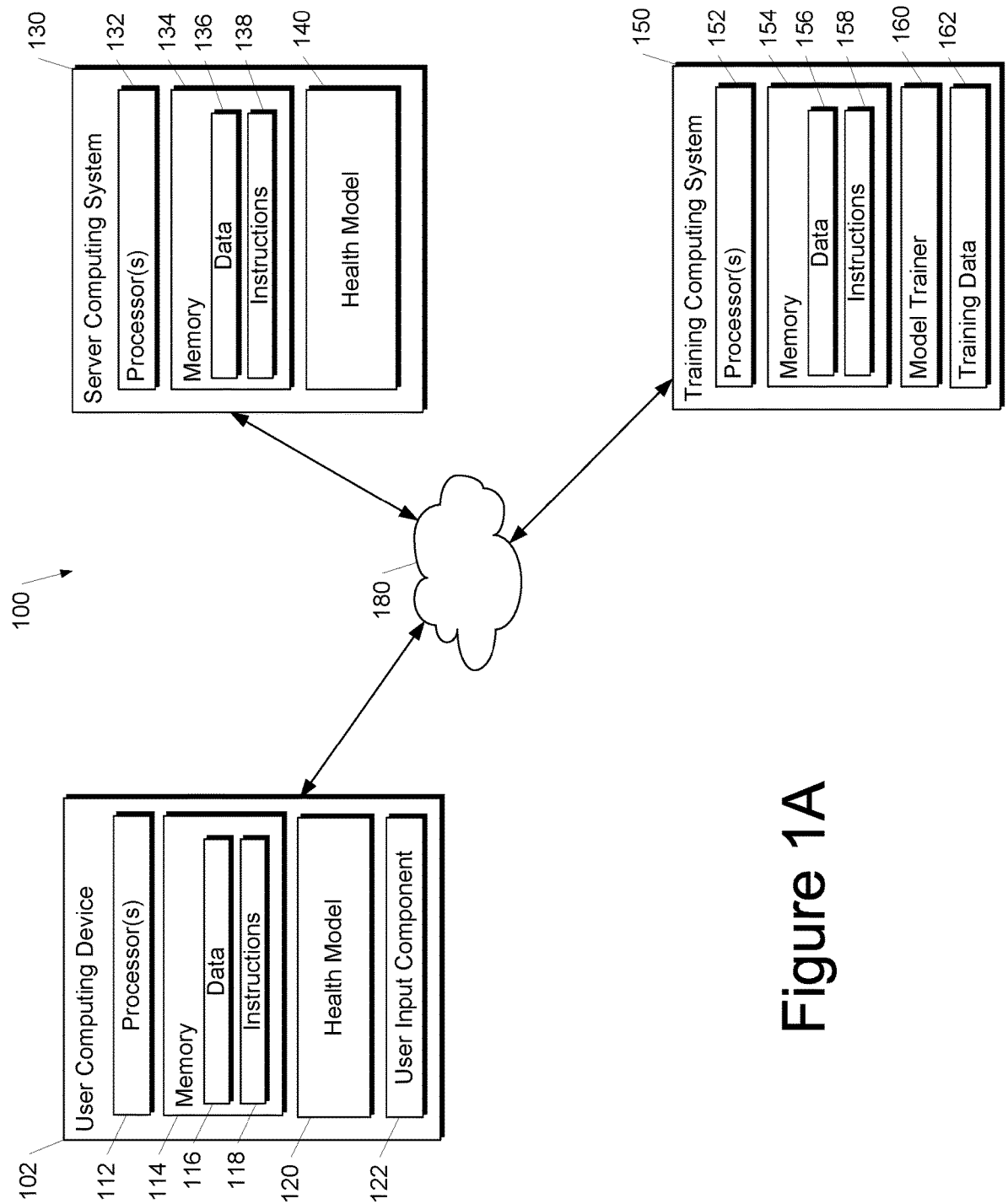
FIG. 1A depicts a block diagram of an example computing system that generates health diagnostic information according to example embodiments of the present disclosure.

Reference numerals that are repeated across plural figures are intended to identify the same features in various implementations.

DETAILED DESCRIPTION

Overview

Generally, the present disclosure is directed to systems and methods that include or otherwise leverage use of a machine-learned health model to provide a diagnosis of a potential health disorder based on an audio recording or other audio data of a patient. In particular, the health model can receive a patient audio recording (e.g., of the patient speaking or making non-word sounds or utterances such as coughing, sneezing, etc.) and, in response, provide a diagnostic score that describes information associated with a potential health disorder. For example, the patient audio recording can contain the patient speaking, and the diagnostic score can contain information about (e.g., identifying, predicting severity of) potential health disorders.

More particularly, systems and methods of the present disclosure can operate to generate or provide health information (e.g., a diagnosis of the existence and/or severity of a particular heath disorder) based on an audio recording of a patient and/or other patient information. The systems and methods of the present disclosure can include or be performed by one or more computing devices, including, as examples, a user computing device (e.g., a smartphone, laptop, computing device able to be worn, an embedded computing device, etc.), a diagnostic computing device (e.g., as operated by a health provider), as a service by a server computing device over a network, and/or other arrangements of computing devices.

These example computing devices can obtain the audio recording of the patient in a number of different ways. As examples, in some implementations, audio data collection can be performed across a constellation of devices that can interoperate, including mobile phones, kiosks/small monitors, desktops, and/or devices that are able to be worn such as headsets and on-attire devices. Importantly, the patient/user can be provided with controls allowing the user to make an election as to both if and when systems, programs or features described herein may enable collection of user information (e.g., audio recordings of the patient's speech). In addition, certain data may be treated in one or more ways before it is stored or used, so that personally identifiable information is removed. For example, a user's identity may be treated so that no personally identifiable information can be determined for the user. Thus, the user may have control over what information is collected about the user, how that information is used, and what information is provided to the user.

According to an aspect of the present disclosure, the systems and methods of the present disclosure can include or otherwise leverage use of a machine-learned health model to provide the diagnosis information. In particular, in some implementations, the health model can include a diagnostic model that is trained to receive the patient audio recording or information describing the patient audio recording (e.g., a spectrogram), and in response, output the diagnostic score. Although referred to as a "recording," it should be understood that in some implementations, the health model can perform real-time analysis on audio data without storing the data. Thus, the term "recording" is used to refer to any audio data, whether stored or analyzed in real time. In some implementations, the health model can additionally include a sound model. In some of such implementations, the sound model can be trained to receive the patient audio recording and, in response to receipt of the patient audio recording, output sound description data that contains information about the patient audio recording. The diagnostic model can be trained to receive the sound description data, and in response to receipt of the sound description data, output the diagnostic score. As an example, each of the sound model and diagnostic model can be or include one or more machine-learned models such as, for example, an artificial neural network ("neural network"), such as, for example, a convolutional neural network.

The diagnostic score can contain information diagnosing or identifying the health disorder. In some implementations, the diagnostic score can describe a predicted severity or likelihood (e.g., of the presence or absence) of a health disorder. As an example, the diagnostic score can describe a predicted severity of amyotrophic lateral sclerosis (ALS). In such an example, the diagnostic score can include a predicted functional rating scale (FRS) score, a metric used in the medical profession to quantify the progression of ALS in patients. As another example, the diagnostic score can describe the severity of a health condition or medical symptom, such as pain. The diagnostic score can describe whether the patient requires urgent medical care or can describe a predicted urgency associated with a need for medical attention.

In some implementations, the diagnostic score can identify a specific health disorder from a set of potential health disorders. As one example, the diagnostic score can include a name or category of one or more health disorder(s) that has been identified based on information contained within the patient audio recording. As another example, the diagnostic score can include a list of two or more potential health disorders, and optionally, associated ranks, likelihoods, severities, etc. Examples of potential health disorders that the health model can be trained to diagnose include cranial nerve dysfunction, depression, autism (e.g., Asperger Syndrome), post-traumatic stress disorder, dementia, ALS, and Parkinson's disease. Additional applications can include identifying and alerting the user about the need for immediate or emergency medical treatment for the patient (e.g., in evaluation phone calls) and/or assessing a pain level experienced by the patient. The health model can find application in identifying or diagnosing any medical condition that manifests itself in the voice of the patient.

According to another aspect of the present disclosure, the sound description data can contain a variety of information about the patient audio recording that can be useful for diagnosing potential health disorders. More particularly, in some implementations, the sound description data can describe sounds (e.g., words, non-word sounds) recognized in the patient audio recording. For example, the sound description data can include a set of word sounds (e.g., words, syllables, phonemes, etc.) that have been recognized (e.g., by the sound model) in the patient audio recording. Such a set of word sounds is sometimes referred to as a "bag of words", "bag of syllables", "bag of phonemes", etc. The sound description data can also include a set of confidence values respectively associated with the set of identified words sounds. As another example, the sound description data can describe a comparison between words recognized in the patient audio recording and a predetermined text string (e.g., a sentence or phrase). For instance, the patient audio recording can contain a recording of the patient reading or otherwise uttering the predetermined text string out loud. The sound model can be trained to recognize the words sounds in the patient audio and output sound description data that describes a comparison between the recognized word sounds and the predetermined text string. For example, the comparison can indicate a number of words or sounds correctly spoken, a percentage of words or sounds correctly spoken, a number or percentage of words or sounds not correctly spoken, a matching score, and/or other forms of comparison. The resulting comparison can be indicative of the patient's ability to intelligibly enunciate specific syllables or phonemes contained in the words of the predetermined text string. As another example, the sound description data can describe a lack of expected sounds (e.g., words, non-word sounds). This information can be indicative of the identity, severity, or likelihood of a potential health disorder.

More specifically, in some implementations, in response to receiving a patient audio recording that indicates difficulty enunciating, the sound model can output a transcript that contains information about such difficulties. As an example, some health disorders (e.g., cranial nerve dysfunction) can impair a patient's ability to properly enunciate a specific set of syllables or to produce certain sequences of syllables or phonemes. This can cause stuttering, variations in vowel and/or consonant sounds, or unintentional pauses between words or syllables indicative of the health disorder. Additionally, in some implementations, the sound description data can describe additional information about speech in the patient audio recording. For example, the sound description data can describe word rate, rhythm, tone, volume, hoarse voice, cadence, syllabic emphasis, pitch, timbre, etc.

In some implementations, the sound description data can include a set of non-word sounds and a set of associated confidence values. As an example, the sound model can be trained to identify a wide variety of non-word sounds, such as coughing or sneezing. As another example, the sound model can be trained to recognize a wide variety of sounds including some that are generally not present in a recording of speech (e.g., musical instruments, doors closing, car engines etc.). Thus, the sound description data can sometimes contain confidence values associated with sounds that are not present in the patient audio recording. Nonetheless, this information can be predictive of health disorders, and thus be useful as an input into the machine-learned diagnostic model (e.g., as contained in the sound description data). This information could be referred to as a sonic "fingerprint" of the patient audio recording or as containing "biomarkers" that may be indicative of certain health states of the speaker.

In some implementations, the sound description data can include an embedding provided by the sound model (e.g., by a final layer and/or a hidden layer of the sound model). As an example, the sound model can include a machine-learned audio classification model, and the sound description data can include an embedding provided by a hidden layer of the machine-learned audio classification model. As such, the embedding can contain information that can be more descriptive of characteristics of the patient audio recording than a simple classification of sounds (e.g., words, non-word sounds) that are recognized in the patient audio recording. This can be particularly useful where, as indicated above, the sound model is trained to recognize sounds that may not be present in a recording of speech (e.g., musical instruments, doors closing, car engines etc.). In such an implementation, the embedding can still contain useful information correlating features of such sounds with sounds in the patient audio recording. Although they may not be correctly identified by the sound model, the embedding can still provide information that is useful for diagnosing the health disorder.

According to another aspect of the present disclosure, in some implementations, the patient audio recording can be divided into segments (e.g., by the sound model or according to a pre-processing scheme), and the segments can be used to generate the diagnostic score. As an example, the patient audio recording can be divided into segments of equal length in time (e.g., 1 second). In some implementations, the segments can be consecutive and non-overlapping. Alternatively, the segments can be overlapping. The sound description data can describe sounds that have been identified (e.g., by the sound model) within one or more of the segments. For example, the sound description data can contain a set of identified sounds (e.g., words, non-words sounds) within the segments. The sound description data can also include a set of confidence values or weights associated with the identified sounds. Sound description data can be generated for each segment individually or can be respectively generated for various combinations of two or more segments (e.g., a combination of every consecutive pair of segments).

A set of segment scores can be generated (e.g., based on the sound description data) that are respectively associated with the set of segments, and the diagnostic score can then be generated based on the set of segment scores. For example, the diagnostic model can generate segment scores for some or all of the segments. The segment scores can be mathematically combined (e.g., averaged) to generate the diagnostic score. As another example, a set of confidence values can be generated (e.g., by the diagnostic model) that are associated with the segment scores. Calculating the diagnostic score can include calculating a weighted average of the segment scores that is weighted according to the set of confidences. Other techniques for combining segment scores can be used as well, including, for example, median techniques, outlier removal techniques, etc.

In some implementations, the health model can include an attention model or an aggregation model that is trained to receive the segment scores, and in response to receiving the segment scores, generate the diagnostic score. As an example, the attention model or aggregation model can be or include a neural network, such a recurrent neural network. In some implementations, the attention or aggregation model can be trained on sequences of segment scores that have been labeled with a known diagnostic score. Thus, the attention or aggregation model can be trained to receive the sequence of segment scores and produce a diagnostic score based on such sequence.

In some implementations, the patient audio recording can be pre-processed. Pre-processing of the patient audio recording can include removing at least one silent or quiet portion of the patient audio recording. For example, quiet or silent portions can be defined as having sound levels below a predetermined threshold level. The health model or other system component can remove such quiet or silent portions before the patient audio recording is input into the sound model, which can improve the performance of the sound model.

According to another aspect of the present disclosure, in some implementations, spectrograms can be generated that describe energy and/or frequency content of the patient audio recording. For example, the spectrograms can characterize the energy distribution across time and frequency of the patient's speech patterns and/or non-speech vocal sounds (e.g. breathing, coughing, wheezing, etc.).

The spectrograms can be input into the sound model and/or diagnostic model (e.g., in addition or alternatively to the raw audio data of the recording). As an example, a spectrogram that describes a set of frequencies and/or corresponding intensities (e.g., sound levels) can be generated and input into the sound model. The spectrogram can be generated using a variety of techniques, including, for example, Fourier transform (e.g., fast Fourier transform, short-time Fourier transform, and/or the like). In some implementations, the spectrograms can be represented in color (e.g., in a color space such as RGB). For example, in some implementations, the audio recording can include multiple channels (e.g., stereo) and can be collected from a plurality of sources (e.g., a microphone array). The spectrograms can describe spatial information associated with the audio recording. The spatial information can be used to identify sources of various sounds in the recording. This may be particularly useful for devices configured to be worn by the user as the spatial information can be used to distinguish between sounds produced by the user or by another nearby audio source. In other implementations, the spectrograms can be represented in grayscale. The sound model can be trained to identify sounds represented by the spectrogram. In some implementations, the spectral features can be augmented with target acoustic parameters characterizing, for example, pitch tracks, spectro-temporal modulation, syllable rate, etc.

According to another aspect of the present disclosure, the health model can be trained to detect changes in diagnosis over time for a given patient. More specifically, in some implementations, the health model can be trained to detect changes in patient audio recordings received at different times for the same patient. As an example, the diagnostic model can be trained to detect changes, such as trends, in the respective sound description data sets associated with the patient audio recordings. Such trends can be indicative of changes in the potential health disorder. As another example, the patient audio recording can be compared against one or more previous audio recordings (e.g., baseline audio recordings) that can represent sonic "fingerprints" or "signatures" of prior collected audio from the same patient. This comparison can be used to detect changes or trends with respect to the previous baseline audio recording(s). In some implementations, the diagnostic model can include a recurrent neural network (e.g., implementing long short term memory techniques). In other embodiments, the health model can include a trend model that is trained to receive diagnostic scores and/or sound description data (e.g., embeddings) from the sound model and/or diagnostic model. The trend model can be trained to output a diagnostic trend score or report containing information that describes changes or trends in the patient audio recordings. As another example, one or more distance metric learning loss functions can be implemented to estimate patient change over time in longitudinal analyses. As yet another example, one or more distributions can be generated that compare diagnostic scores or intermediary data (e.g., sound description data) to observed normal ranges for each particular patient.

According to another aspect of the present disclosure, the health model can be trained to identify a specific patient or speaker from the patient audio recording. More specifically, in some implementations, the health model can be trained to identify portions of the patient audio recording in which the patient seeking a diagnostic score is speaking. This capability can be particularly useful for detecting diagnostic trends, as discussed above.

In some implementations, the health model can be trained using supervised training techniques. A training data set can include a set of training recordings and a set of training diagnoses associated with the training recordings. The set of training recordings can include recordings of patients speaking and/or making non-word sounds, and the set of training diagnosis can include information about health disorders (e.g., identity, severity, etc.) associated with the patients. The training data can be input into the health model, and diagnostic scores can be output by the health model in response. The training recordings can also include labeled non-patient audio recordings. For example, in some implementations, sets of publically available, labeled audio training data can be used to pre-train the sound model to recognize word sounds and/or non-word sounds.

One or more objective functions (e.g., loss functions) can be calculated that describe a comparison between the output of the health model (e.g., diagnostic scores) and the labels/training data (e.g., training diagnoses). A training computing system can use the objective function(s) to train the sound model, diagnostic model, and/or attention or aggregation model by adjusting (e.g., iteratively) parameters of the health model such that evaluations of the objective function(s) move towards a target value (e.g., to minimize a loss function). As an example, loss function weighting can be implemented to correct/adjust for class imbalance in the training data that is often present in medical datasets.

Additionally, in some implementations, the health model can be trained using unsupervised learning techniques. For example, the sound model can be pre-trained using unlabeled non-patient collections of sound recordings, such as speech recordings, non-speech sounds, publically available sound recordings from online video, etc. For instance, the sound model can start as a general purpose word and/or sound recognition model. Additionally, the diagnosis model can be pre-trained using sound description data generated from the sound model during pre-training. This pre-training using unlabeled non-patient collections of sound recordings may reduce the number of labelled patient sound recordings that are required in order to obtain a certain degree of accuracy/reliability from the health model.

Providing diagnostic information about potential health disorders from a patient audio recording can have many uses. As an example, patients can record themselves using a personal computing device (e.g., smartphone, tablet, personal computer etc.) at their convenience, such as in their own home. The health model may be able to provide the patient with a fast and efficient initial indication of potential health disorders for further investigation. Indeed, the health model may enable determination of the presence of certain disorders in a manner that is non-invasive. In addition, use of the health model may allow disorders to be detected based on indications that are too subtle for conventional methods to detect. As such, the health model may enable disorders to be detected at an earlier stage. As another example, health professionals (e.g., nurses, doctors) can leverage use of the health model in a clinical setting, such as a doctor's office or hospital, to aid in identifying potential health disorders for further investigation.

As one example, the systems and methods of the present disclosure can be included or otherwise employed within the context of an application, a browser plug-in, or in other contexts. Thus, in some implementations, the models of the present disclosure can be included in or otherwise stored and implemented by a user computing device such as a laptop, tablet, or smartphone. As yet another example, the models can be included in or otherwise stored and implemented by a server computing device that communicates with the user computing device according to a client-server relationship. For example, the models can be implemented by the server computing device as a portion of a web service (e.g., a health assessment service).

With reference now to the Figures, example embodiments of the present disclosure will be discussed in further detail.

Example Devices and Systems

FIG. 1A depicts a block diagram of an example computing system 100 that provides a diagnosis of a potential health disorder based on an audio recording of a patient according to example embodiments of the present disclosure. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, a FPGA, a controller, a microcontroller, etc.) and can be one processor or a plurality of processors that are operatively connected. The memory 114 can include one or more non-transitory computer-readable storage mediums, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

The user computing device 102 can store or include one or more health models 120. For example, the health models 120 can be or can otherwise include various machine-learned models such as neural networks (e.g., deep neural networks) or other multi-layer non-linear models. Neural networks can include recurrent neural networks (e.g., long short-term memory recurrent neural networks), feed-forward neural networks, convolutional neural networks, or other forms of neural networks. Alternatively or additionally, the health model can include one or more other forms of machine-learned models such as, as examples, classifier models (e.g., linear classification models, quadratic classification models, binary classifiers, multi-class classifiers, multi-label classifiers, etc.); one or more regression models (e.g., simple linear regression models, multiple linear regression models, logistic regression models, stepwise regression models, multivariate adaptive regression splines, locally estimated scatterplot smoothing models, etc.); one or more decision tree-based models (e.g., classification and/or regression trees, iterative dichotomiser 3 decision trees, C4.5 decision trees, chi-squared automatic interaction detection decision trees, decision stumps, conditional decision trees, etc.); one or more kernel machines; one or more support vector machines; one or more nearest neighbor models (e.g., k-nearest neighbor classifications models, k-nearest neighbors regression models, etc.); one or more Bayesian (e.g., naïve Bayes models, Gaussian naïve Bayes models, multinomial naïve Bayes models, averaged one-dependence estimators, Bayesian networks, Bayesian belief networks, hidden Markov models, etc.); and/or other forms of models. Example health models 120 are discussed with reference to FIGS. 2-6.

In some implementations, the one or more health models 120 can be received from the server computing system 130 over network 180, stored in the user computing device memory 114, and the used or otherwise implemented by the one or more processors 112. In some implementations, the user computing device 102 can implement multiple parallel instances of a single health model 120 (e.g., to perform parallel processing of audio and/or subsequent analysis across multiple instances of the health model).

More particularly, the health model 120 can receive a patient audio recording (e.g., of the patient speaking or making non-word sounds such as coughing, sneezing, etc.) and, in response, provide a diagnostic score that describes information associated with a potential health disorder. For example, the patient audio recording can contain the patient speaking, and the diagnostic score can contain information about (e.g., identifying, predicting severity of) potential health disorders.

Additionally or alternatively, one or more health models 140 can be included in or otherwise stored and implemented by the server computing system 130 that communicates with the user computing device 102 according to a client-server relationship. For example, the health models 140 can be implemented by the server computing system 140 as a portion of a web service (e.g., a health disorder diagnostic web service). Thus, one or more models 120 can be stored and implemented at the user computing device 102 and/or one or more models 140 can be stored and implemented at the server computing system 130.

The user computing device 102 can also include one or more user input component 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can enter a communication.

The server computing system 130 includes one or more processors 132 and a memory 134. The one or more processors 132 can be any suitable processing device (e.g., a processor core, a microprocessor, an ASIC, a FPGA, a controller, a microcontroller, etc.) and can be one processor or a plurality of processors that are operatively connected. The memory 134 can include one or more non-transitory computer-readable storage mediums, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise includes one or more machine-learned health models 140. For example, the models 140 can be or can otherwise include various machine-learned models such as neural networks (e.g., deep recurrent neural networks) or other multi-layer non-linear models or other forms of models as described with reference to models 120. Example models 140 are discussed with reference to FIGS. 2-6.

The server computing system 130 can train the models 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, a FPGA, a controller, a microcontroller, etc.) and can be one processor or a plurality of processors that are operatively connected. The memory 154 can include one or more non-transitory computer-readable storage mediums, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 140 stored at the server computing system 130 using various training or learning techniques, such as, for example, backwards propagation of errors. In some implementations, performing backwards propagation of errors can include performing truncated backpropagation through time. The model trainer 160 can perform a number of generalization techniques (e.g., weight decays, dropouts, etc.) to improve the generalization capability of the models being trained.

In particular, the model trainer 160 can train a health model 140 based on a set of training data 142. The training data 142 can include, for example, a set of training recordings and a set of training diagnoses associated with the training recordings. The set of training recordings can include recordings of patients speaking and/or making non-word sounds (e.g., coughing, sneezing, sniffling, laughing, etc.) and the set of training diagnosis can include information about health disorders (e.g., identity, severity, etc.) associated with the patients. The training data can be input into the health model, and diagnostic scores can be output by the health model in response. The training recordings can also include labeled non-patient audio recordings. For example, sets of publically available, labeled audio training data can be used to pre-train the sound model to recognize word sounds and/or non-word sounds.

In some implementations, if the user has provided consent, the training examples can be provided by the user computing device 102 (e.g., based on communications previously provided by the user of the user computing device 102). Thus, in such implementations, the model 120 provided to the user computing device 102 can be trained by the training computing system 150 on user-specific communication data received from the user computing device 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory and executed by one or more processors. In other implementations, the model trainer 160 includes one or more sets of computer-executable instructions that are stored in a tangible computer-readable storage medium such as RAM hard disk or optical or magnetic media.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 1A illustrates one example computing system that can be used to implement the present disclosure. Other computing systems can be used as well. For example, in some implementations, the user computing device 102 can include the model trainer 160 and the training dataset 162. In such implementations, the models 120 can be both trained and used locally at the user computing device 102. In some of such implementations, the user computing device 102 can implement the model trainer 160 to personalize the models 120 based on user-specific data.

Figure 1B:
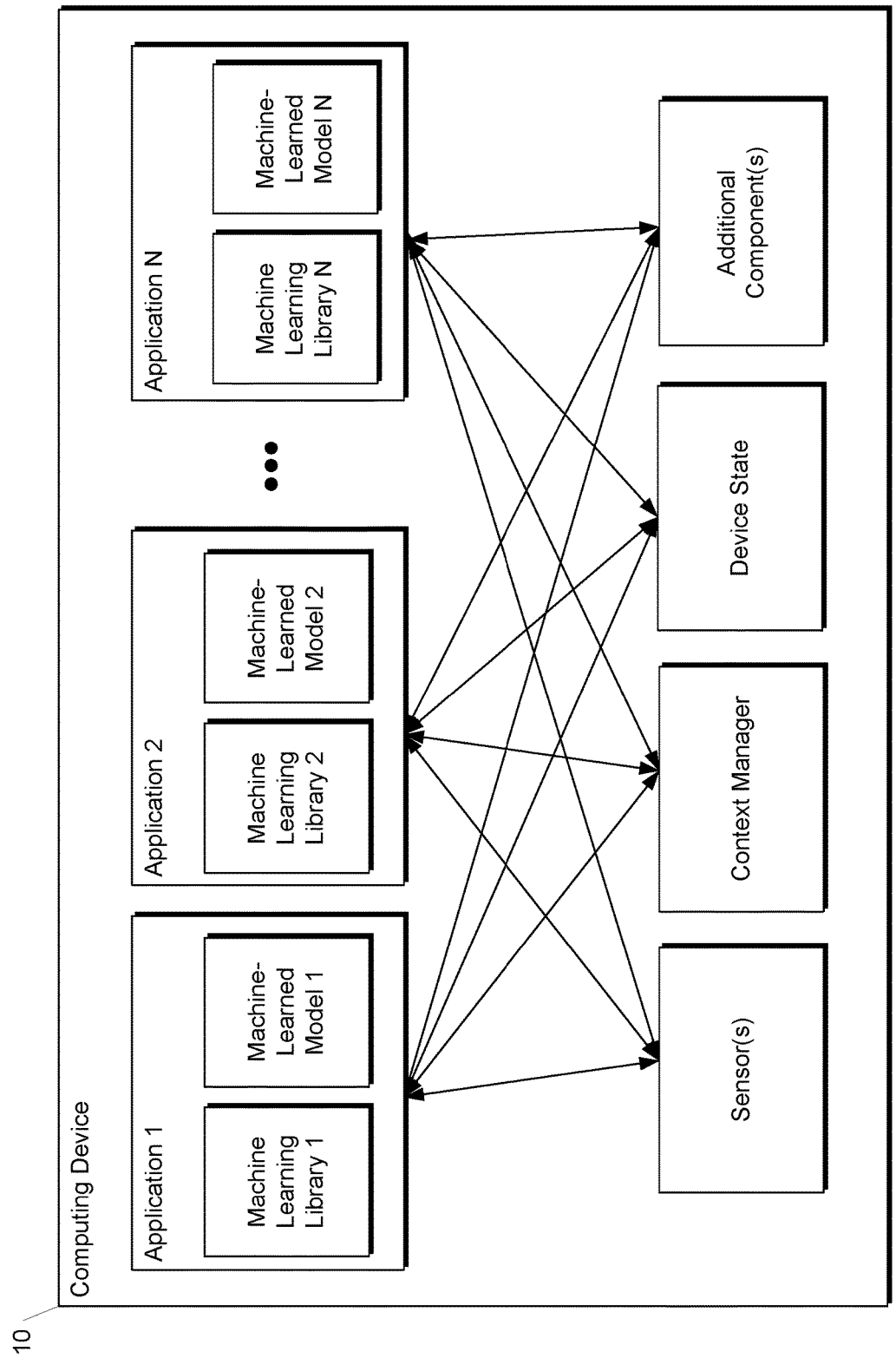
FIG. 1B depicts a block diagram of an example computing device that generates health diagnostic information according to example embodiments of the present disclosure.

FIG. 1B depicts a block diagram of an example computing device 10 that performs according to example embodiments of the present disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 1B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 1C:
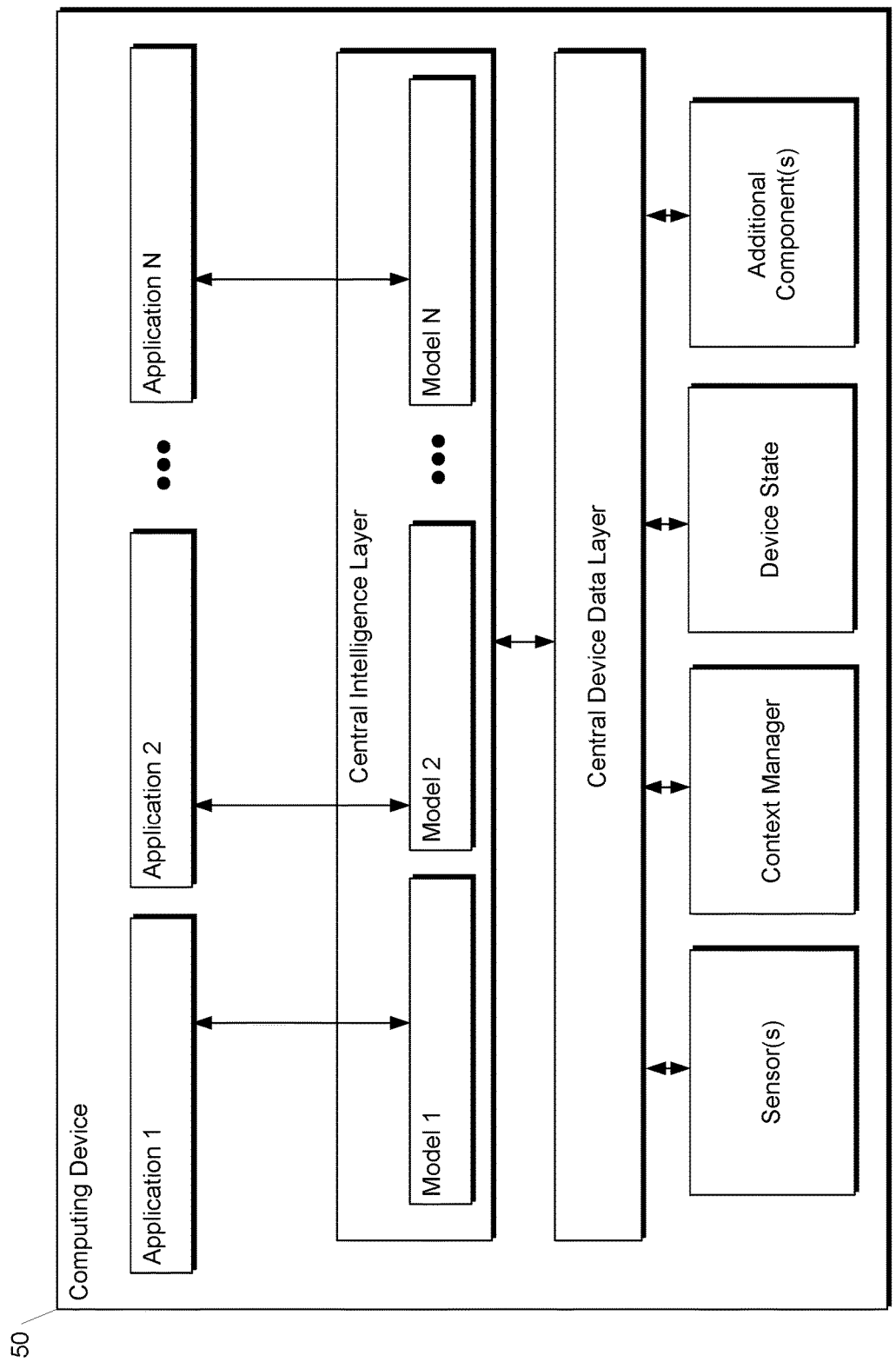
FIG. 1C depicts a block diagram of an example computing device that generates health diagnostic information according to example embodiments of the present disclosure.

FIG. 1C depicts a block diagram of an example computing device 50 that performs according to example embodiments of the present disclosure. The computing device 50 can be a user computing device or a server computing device.

The computing device 50 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 1C, a respective machine-learned model (e.g., a model) can be provided for each application and managed by the central intelligence layer. In other implementations, two or more applications can share a single machine-learned model. For example, in some implementations, the central intelligence layer can provide a single model (e.g., a single model) for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 1C, the central device data layer can communicate with a number of other components of the computing device, such as, for example, one or more sensors, a context manager, a device state component, and/or additional components. In some implementations, the central device data layer can communicate with each device component using an API (e.g., a private API).

Example Model Arrangements

FIG. 2 depicts a block diagram of an example health model 200 according to example embodiments of the present disclosure. In some implementations, the health model 200 can include a diagnostic model 202 that is trained to receive a patient audio recording 204 (e.g., of the patient speaking or making non-word sounds such as coughing, sneezing, etc.) or data descriptive of the patient audio recording (e.g., one or more spectrogram 206) and, in response, provide a diagnostic score 208. The diagnostic model 202 can be or otherwise include a neural network (e.g., a convolutional neural network).

The diagnostic score 208 can contain information diagnosing or identifying the health disorder. For example, the diagnostic score 208 can describe a predicted severity of amyotrophic lateral sclerosis (ALS). For instance, the diagnostic score 208 can include a predicted functional rating scale (FRS) score, a metric used in the medical profession to quantify the progression of ALS in patients. As another example, the diagnostic score 208 can describe the severity of a health condition or medical symptom, such as pain. The diagnostic score can describe whether the patient requires urgent medical care or can describe a predicted urgency associated with a need for medical attention.

In some implementations, the diagnostic score 208 can identify a specific health disorder from a set of potential health disorders. As one example, the diagnostic score 208 can include a name or category of one or more health disorder(s) that has been identified based on information contained within the patient audio recording. As another example, the diagnostic score 208 can include a list of two or more potential health disorders, and optionally, associated ranks, likelihoods, severities, etc. Examples of potential health disorders that the health model 200 can be trained to diagnose include cranial nerve dysfunction, depression, autism (e.g., Asperger Syndrome), post-traumatic stress disorder, dementia, ALS, and Parkinson's disease. Additional applications can include the need for immediate or emergency medical treatment for the patient (e.g., in evaluation phone calls) and assessing a pain level experienced by the patient (e.g. using "gold standard" Revised Faces Scale or NRS numeric rating scale "zero to ten"). The health model 200 can find application in identifying or diagnosing any medical condition that manifests itself in the voice of the patient, however.

The spectrogram(s) 206 can describe energy and/or frequency content of the patient audio recording 204. For example, the spectrograms 206 can characterize the energy distribution across time and frequency of the patient's speech patterns and/or non-speech vocal sounds (e.g. breathing, coughing, wheezing, etc.).

The spectrograms 206 can be input into the diagnostic model 202 (e.g., in addition or alternatively to the raw audio data of the patient audio recording 204). The spectrogram 206 can be generated using a variety of techniques, including, for example, Fourier transform (e.g., fast Fourier transform, short-time Fourier transform, and/or the like). In some implementations, the spectrograms 206 can be represented in color (e.g., in a color space such as RGB). In other implementations, the spectrograms 206 can be represented in grayscale. The diagnostic model 202 can be trained to generate diagnostic information in the diagnostic score 208 based on the information contained in the spectrogram(s) 206.

In some implementations, the patient audio recording 204 can be pre-processed. Pre-processing of the patient audio recording 204 can include removing at least one silent or quiet portion of the patient audio recording 204. For example, quiet or silent portions can be defined as having sound levels below a predetermined threshold level. The health model 200 can remove such quiet or silent portions before the patient audio recording is input into the diagnostic model 202, which can improve the performance of the diagnostic model 202.

FIG. 3 depicts a block diagram of an example health model 300 according to example embodiments of the present disclosure. The health model 300 is similar to the health model 200 of FIG. 2 except that health model 300 further includes a sound model 302. The sound model 302 can be or otherwise include a neural network (e.g., a convolutional neural network). The sound model 302 can be trained to receive the patient audio recording 306 and/or data descriptive thereof (e.g., spectrogram(s) 308) and, in response, output sound description data 310 that contains information about the patient audio recording 306. The diagnostic model 304 can be trained to receive the sound description data 310, and in response to receipt of the sound description data 310, output the diagnostic score 312.

In some implementations, the spectrogram(s) 308 can be input into the sound model 302. In other implementations, the spectrogram(s) 308 can be input into both the sound model 302 and the diagnostic model 304. As an example, a spectrogram 206 that describes a set of frequencies and/or corresponding intensities (e.g., sound levels) can be generated and input into the sound model 302. The sound model 302 can be trained to identify sounds represented by the spectrogram 308. For example, the sound model 302 can be trained to output sound description data 310 that describes features of the patient audio recording 306. The spectral features of the patient audio recording 306 can be augmented with target acoustic parameters characterizing, for example, pitch tracks, spectro-temporal modulation, syllable rate, etc.

Additional pre-processing can include removing quiet or silent portions of the patient audio recording 306, for example as described above with reference to FIG. 2. The health model 300 can remove such quiet or silent portions before the patient audio recording is input into the sound model 302, for example, which can improve the performance of the sound model 302.

In some implementations, the sound description data 310 can contain a variety of information about the patient audio recording 306 that can be useful for diagnosing potential health disorders. More particularly, in some implementations, the sound description data 310 can describe sounds (e.g., words, non-word sounds) recognized in the patient audio recording 306. For example, the sound description data 310 can include a set of word sounds (e.g., words, syllables, phonemes, etc.) that have been recognized (e.g., by the sound model 302) in the patient audio recording 306. Such a set of word sounds is sometimes referred to as a "bag of words", "bag of syllables", "bag of phonemes", etc. The sound description data 310 can also include a set of confidence values associated with the set of identified words sounds. As another example, the sound description data 310 can describe a comparison between words recognized in the patient audio recording 306 and a predetermined text string (e.g., a sentence or phrase). For instance, the patient audio recording 306 can contain a recording of the patient uttering the predetermined text string out loud. The sound model 302 can be trained to recognize the word sounds in the patient audio recording 306 and output sound description data 310 that describes a comparison between the recognized word sounds and the predetermined text string. The resulting comparison can be indicative of the patient's ability to intelligibly enunciate specific syllables or phonemes contained in the words of the predetermined text string. This information can be indicative of the identity, severity, or likelihood of a potential health disorder, for example.

More specifically, in response to receiving a patient audio recording 306 that indicates difficulty enunciating, the sound model 302 can output sound description data 310 that contains information about such difficulties. As an example, some health disorders (e.g., cranial nerve dysfunction) can impair a patient's ability to properly enunciate a specific set of syllables or to produce certain sequences of syllables or phonemes. This can cause stuttering, variations in vowel and/or consonant sounds, or unintentional pauses between words or syllables indicative of the health disorder. Additionally, in some implementations, the sound description data 310 can describe additional information about speech in the patient audio recording 306. For example, the sound description data 310 can describe word rate, rhythm, tone, volume, hoarse voice etc.

In some implementations, the sound description data 310 can include a set of non-word sounds and a set of associated confidence values. As an example, the sound model 302 can be trained to identify a wide variety of non-word sounds, such as coughing or sneezing. As another example, the sound model 302 can be trained to recognize a wide variety of sounds including some that are generally not present in a recording of speech. Examples of such sounds include musical instruments, doors closing, car engines. Thus, the sound description data 310 can sometimes contain confidence values associated with sounds that are not present in the patient audio recording 306. Nonetheless, this information can be predicative of health disorders, and thus be useful as an input into the machine-learned diagnostic model 304. This information could be referred to as a sonic "fingerprint" of the patient audio recording or as "biomarkers" that may be indicative of certain health states of the speaker.

In some implementations, the sound description data 310 can include an embedding provided by a hidden layer of the sound model 302. As an example, the sound model 302 can include a machine-learned audio classification model, and the sound description data 302 can include an embedding by a hidden layer of the machine-learned audio classification model. As such, the embedding can contain information that can be more descriptive of characteristics of the patient audio recording 306 than a simple classification of sounds (e.g., words, non-word sounds) that are recognized in the patient audio recording 306. This can be particularly useful where, as indicated above, the sound model 302 is trained to recognize sounds that may not be present in a recording of speech (e.g., musical instruments, doors closing, car engines etc.). In such an implementation, the embedding can still contain useful information correlating features of such sounds with sounds in the patient audio recording 306. Although these sounds may not be correctly identified by the sound model 302, the embedding can still provide information that is useful for diagnosing the health disorder.

According to another aspect of the present disclosure, in some implementations, the patient audio recording 306 can be divided into segments (e.g., by the sound model 302), and the segments can be used to generate the diagnostic score 312. As an example, the patient audio recording 306 can be divided into segments of equal length in time (e.g., 1 second). In some implementations, the segments can be consecutive and non-overlapping. Alternatively, the segments can be overlapping. The sound description data 310 can describe sounds that have been identified or correlated (e.g., by the sound model 302) within two or more of the segments. For example, the sound description data 310 can contain a set of identified sounds (e.g., words, non-words sounds) within the segments. The sound description data 310 can also include a set of confidence values or weights associated with the identified sounds. Alternatively, a separate sound description data set 310 can be generated for each individual segment.

A set of segment scores can be generated that are respectively associated with the set of segments, and the diagnostic score can then be generated based on the set of segment scores. For example, the diagnostic model 304 can generate segment scores for some or all of the segments represented in the sound description data 310. The segment scores can be mathematically combined (e.g., averaged) to generate the diagnostic score 312. As another example, a set of confidence values can be generated (e.g., by the diagnostic model 304) that are associated with the segment scores. Calculating the diagnostic score 312 can include calculating a weighted average of the segment scores that is weighted according to the set of confidences. Other techniques for combining segment scores can be used as well, including, for example, median techniques, outlier removal techniques, etc.

Figure 4:
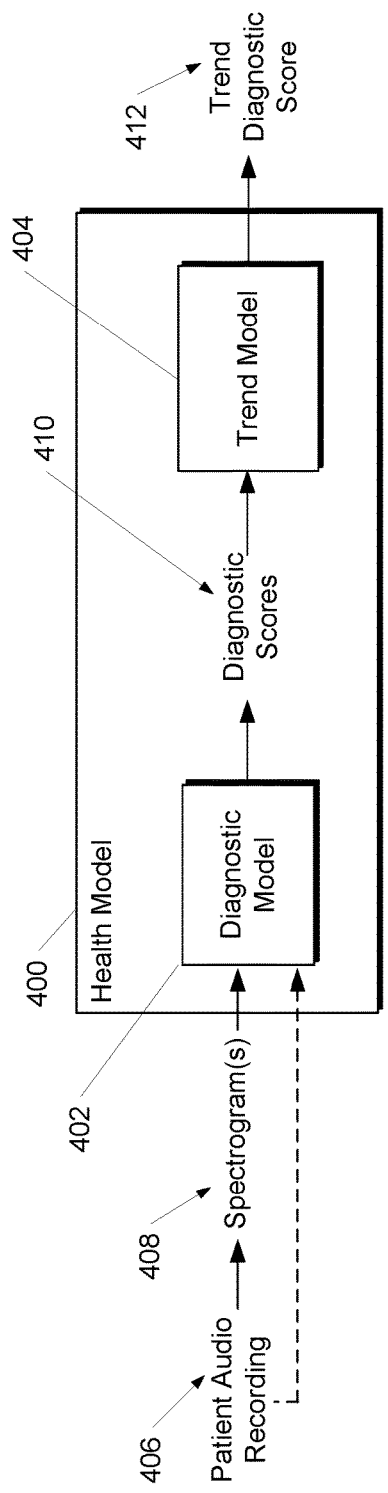
FIG. 4 depicts a block diagram of an example health model according to example embodiments of the present disclosure.

FIG. 4 depicts a block diagram of an example health model 400 according to example embodiments of the present disclosure. The health model 400 is similar to the health model 200 of FIG. 2 except that health model 400 further includes a trend model 404. The trend model 404 can be or include a neural network, such a recurrent neural network (e.g., long short-term memory recurrent neural networks). The trend model 404 can be trained to receive two or diagnostic scores 410 from the diagnostic model 403 and, in response to receiving the diagnostic scores 410 output a trend diagnostic score 412 or report that contains information describing changes or trends in the diagnostic scores 410 output by the diagnostic model 402. For example, the trend model 404 can be trained to recognize changes in the diagnostic scores 410 that are indicative of progression of a health disorder. The health model 400 may be configured to alert the user of trend diagnostic scores 412 that warrant further investigation.

According to another aspect of the present disclosure, the health model 400 can be trained to identify a specific patient or speaker from the patient audio recording 406. More specifically, in some implementations, the health model 400 can be trained to identify portions of the patient audio recording 406 in which the particular patient that is seeking diagnostic information is speaking (e.g., the owner of the device collecting the audio recording). This capability can be particularly useful for detecting diagnostic trends, as discussed above.

Figure 5:
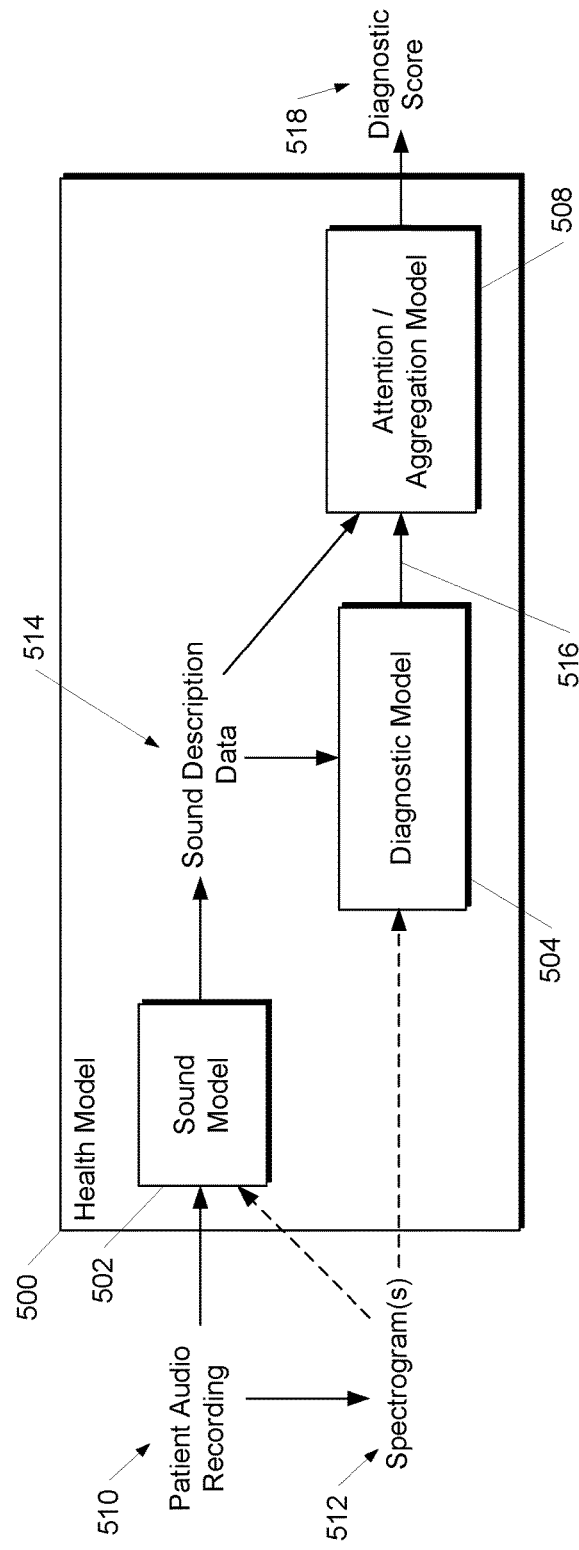
FIG. 5 depicts a block diagram of an example health model according to example embodiments of the present disclosure.

FIG. 5 depicts a block diagram of an example health model 500 according to example embodiments of the present disclosure. The health model 500 is similar to the health model 300 of FIG. 3 except that health model 500 further includes an attention or aggregation model 508. As an example, the attention model or aggregation model 508 can be or include a neural network, such a recurrent neural network.

In this implementation, the patient audio recording 510 can be divided into segments (e.g., by the sound model 502), and the segments can be used to generate the diagnostic score 518. For example, the sound description data 514 can describe sounds that have been identified or correlated (e.g., by the sound model 502) within two or more of the segments, for example as explained above with reference to FIG. 3. The diagnostic model 504 can be trained to receive the sound description data 514 and/or other data descriptive of the patient audio recording (e.g., spectrogram(s) 512), and in response, output segment scores 516 for some or all of the segments represented in the sound description data 514. The attention/aggregation model 508 can be trained to receive the segment scores 516 and/or sound description data 514 and in response, output the diagnostic score 518. For example, the attention/aggregation model 508 can be trained to "focus" on or weight the segments scores 516 and/or associated sound description data 514 that are most indicative of potential health disorders. This implementation can provide a more predicative aggregation of the segment scores than simple averaging or weighted averaging described above with reference to FIG. 3.

Additionally, in some implementations, the health model 500 can leverage the attention/aggregation model 508 to improve performance of the sound model 502 and/or diagnostic model 504. For example, the attention/aggregation model 508 can generate an attention output that describes the relative importance of data segments. One or both of the sound model 502 or diagnostic model 504 can be trained to receive the attention output and "focus" on the most relevant segments of patient audio recording 510 and/or associated sound description data 514. For example, the sound model 502 and/or diagnostic model 504 can allocate resources at least partially according to the attention output. As another example, the sound model 502 and/or diagnostic model 504 can adjust weights associated with the various segments based on the attention output (e.g., increasing the weights for the most relevant segments).

Figure 6:
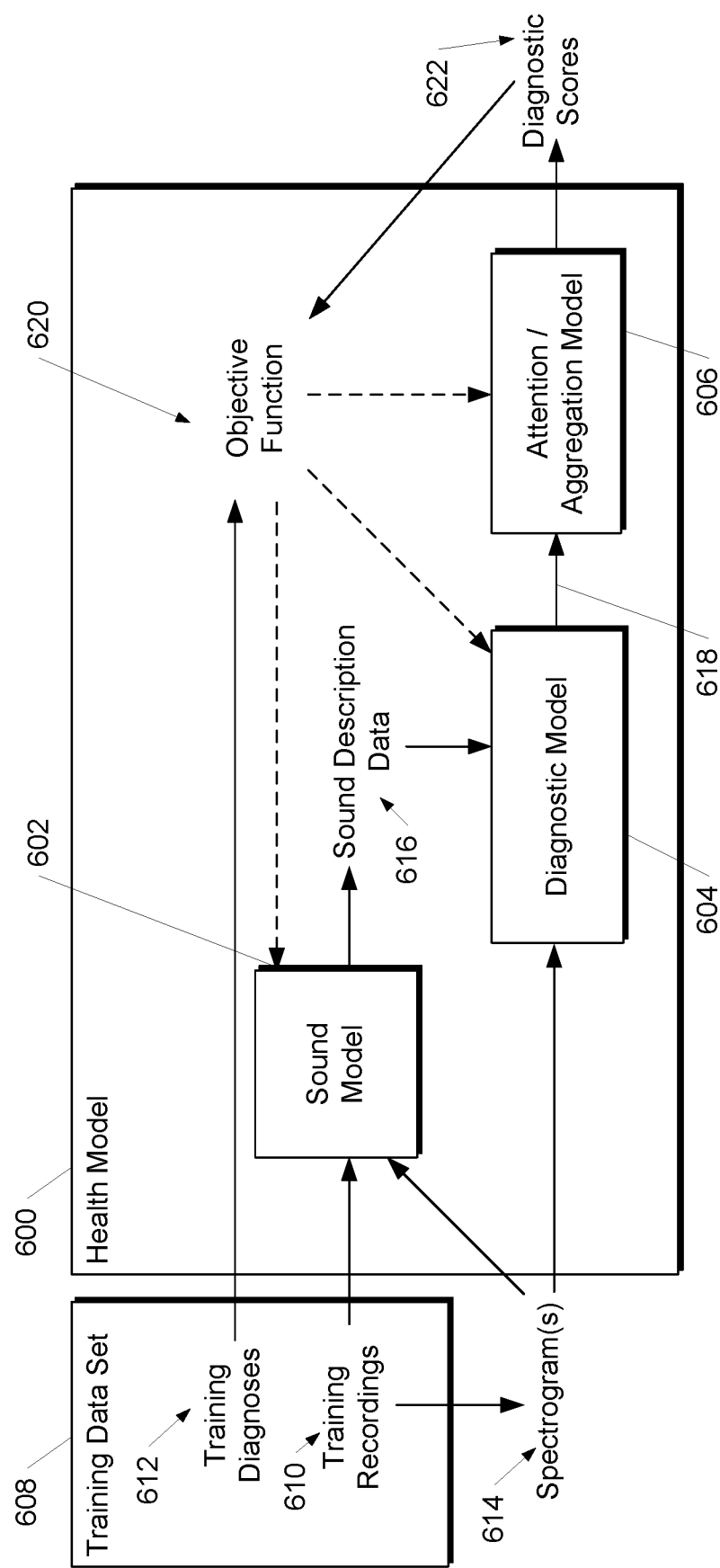
FIG. 6 depicts a block diagram of an example health model according to example embodiments of the present disclosure.

FIG. 6 depicts a block diagram of an example health model 600 configured to receive a training data set 608 according to example embodiments of the present disclosure. The training data set can include a set of training recordings 610 and a set of training diagnoses 612 associated with the training recordings 610. The set of training recordings 610 can include recordings of patients speaking and/or making non-word sounds, and the set of training diagnosis 612 can include information about health disorders (e.g., identity, severity, etc.) associated with the patients. The training data set 608 can be input into the health model 600, and diagnostic scores 622 can be output by the health model 600 in response. The training recordings 610 can also include labeled non-patient audio recordings. For example, sets of publically available, labeled audio training data can be used to pre-train the sound model to recognize word sounds and/or non-word sounds.

One or more objective functions 620 (e.g., loss functions) can be calculated that describe a comparison between the output of the health model (e.g., diagnostic scores 622) and the labels/training data (e.g., training diagnoses 612). The object function(s) 620 can be used to iteratively train the sound model 602, diagnostic model 604, and/or attention/aggregation model 606 (and trend model if present) by seeking to adjust the objective function 620 to a target value (e.g., to minimize a loss function). As an example, loss function weighting can be implemented to correct/adjust for class imbalance in the training data set 608 that is often present in medical datasets.

Additionally, in some implementations, the health model 600 can be trained using unsupervised learning techniques. For example, the sound model 600 can be pre-trained using unlabeled non-patient collections of sound recordings, such as speech recordings, non-speech sounds, publically available sound recordings from online video, etc. For instance, the sound model 600 can start as a general purpose word and/or sound recognition model. Additionally, the diagnosis model 604 can be pre-trained using sound description data 616 generated from the sound model during pre-training. Similarly, the attention/aggregation model 606 can be pre-trained using output 618 (e.g., segment scores) from the diagnostic model 604 during pre-training.

Example Methods

Figure 7:
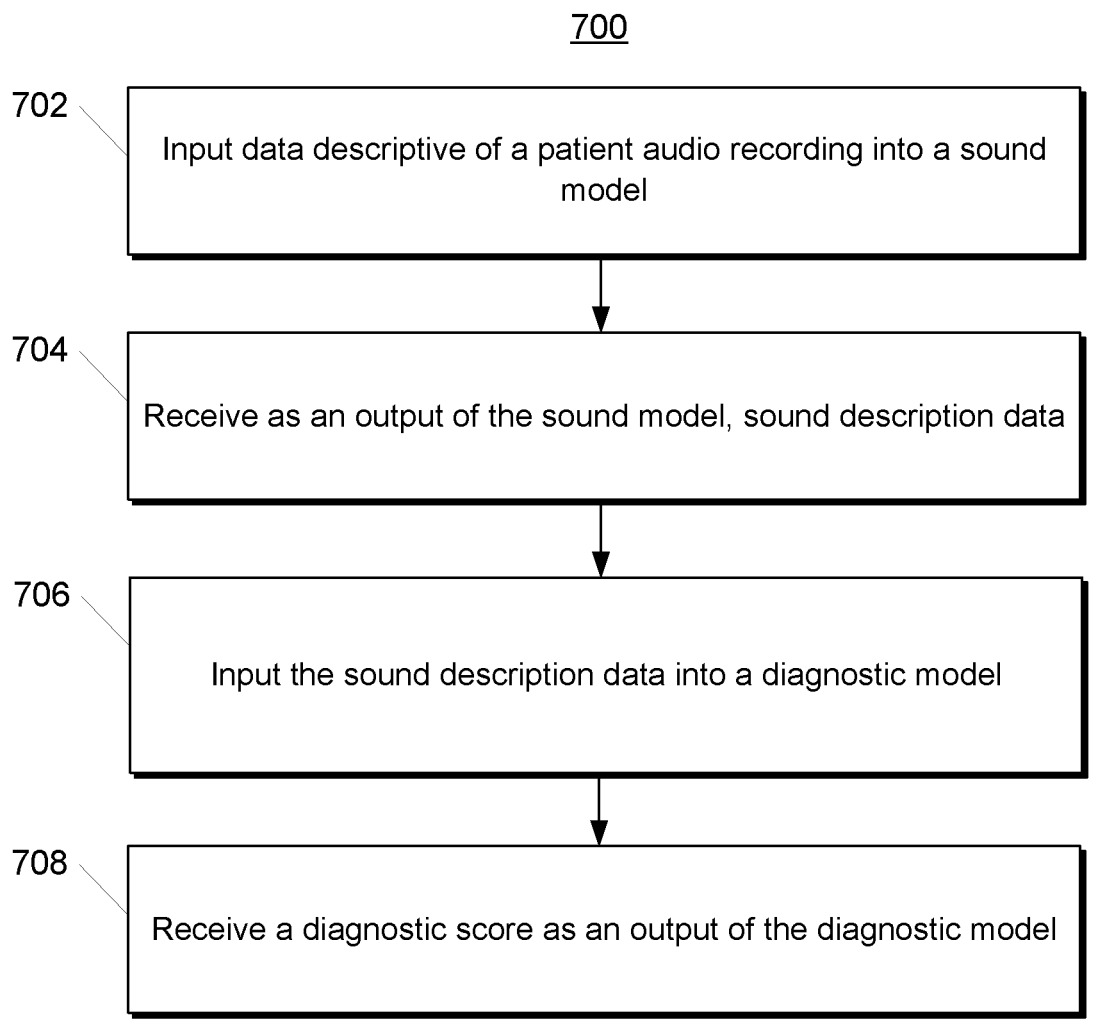
FIG. 7 depicts a flow chart diagram of an example method to perform generate diagnostic information according to example embodiments of the present disclosure.

FIG. 7 depicts a flow chart diagram of an example method to perform according to example embodiments of the present disclosure. Although FIG. 6 depicts steps performed in a particular order for purposes of illustration and discussion, the methods of the present disclosure are not limited to the particularly illustrated order or arrangement. The various steps of the method 700 can be omitted, rearranged, combined, and/or adapted in various ways without deviating from the scope of the present disclosure.

At 702, a computing system can input data descriptive of a patient audio recording into a sound model. The patient audio recording can first be obtained by one or more computing devices of the computing system. For example, audio data collection can be performed across an interconnected and/or interoperable array of devices (e.g., mobile phones, kiosks/small monitors, desktops, or wearable devices such as headsets and on-attire devices). Importantly, the patient/user can be provided with controls allowing the user to make an election as to both if and when systems, programs or features described herein may enable collection of user information (e.g., audio recordings of the patient's speech). In addition, certain data may be treated in one or more ways before it is stored or used, so that personally identifiable information is removed.

In response to recording or otherwise receiving the patient audio recording, the computing system can provide the input to the sound model. The patient audio recording can include word sounds or non-word sounds uttered or otherwise produced by the patient or user.

At 704, the computing system can receive as an output of the sound model, sound description data. For example, the sound description data can describe correlations or similarities between features of the patient audio recording data and known sounds (e.g., as an embedding from a sound recognition model).

At 706, the computing system can input the sound description data into a diagnostic model. At 708, the computing system can receive a diagnostic score as an output of the diagnostic model. For example, the diagnostic score can describe an identity of a specific health disorder from a potential set of health disorders, a likelihood of the patient having a specific health disorder, and/or a predicted severity of the specific health disorder.

Example Application

The health model may find particular application with health disorders that affect speaking abilities. For example, as discussed above, the health model can be trained to generate a diagnostic score that describes a predicted severity of amyotrophic lateral sclerosis (ALS). In such an example, the diagnostic score can include a predicted functional rating scale (FRS) score. FRS is a metric used in the medical profession to quantify the progression of ALS in patients and ranges from 0 to 4.

The health model was used to generate predicted FRS scores from patient audio recordings of ALS patients. The predicted FRS scores were then compared with known FRS scores for each patient. The recordings were converted into spectrograms, which describe frequency and energy information associated with the patient audio recordings. The recordings were also divided into consecutive, non-overlapping, segments of equal length. In this example, the segments were one second long. The recordings and spectrograms were input into the health model, and segment scores were received as an output of the health model. The segment scores included a set of scores and confidence values respectively associated with each segment. The segment scores were combined according to their respective confidence values (e.g., using a weighted average) to produce the diagnostic scores. The diagnostic scores described FRS scores for each respective audio recording.

In one set of analyses, the health model had an average prediction error of the known FRS score of 0.6. Ninety eight percent of the predicted FRS scores were within one unit of the known FRS scores. This corresponds to a class balanced accuracy of 64% in a dataset of 715 patients, an Area Under Curve (AUC) of 0.90, and a sensitivity index (d') of 1.8. These metrics, which are used in signal detection theory, indicate that the health model produced high quality FRS score predictions. Additionally, the health model was found to accurately predict the progression of disease within individual patients.

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computing system, comprising:
at least one processor;
a machine-learned health model comprising:
a sound model, wherein the sound model is trained to receive data descriptive of a patient audio recording and, in response to receipt of the patient audio recording, output sound description data, wherein the sound model comprises a machine-learned audio classification model, and wherein the sound description data comprises an embedding provided by a hidden layer of the machine-learned audio classification model; and
a diagnostic model, wherein the diagnostic model is trained to receive the sound description data, and in response to receipt of the sound description data, output a diagnostic score; and
at least one tangible, non-transitory computer-readable medium that stores instructions that, when executed by the at least one processor, cause the at least one processor to perform operations, the operations comprising:
obtaining the patient audio recording;
inputting data descriptive of the patient audio recording into the sound model;
receiving, as an output of the sound model, the sound description data;
inputting the sound description data into the diagnostic model; and
receiving, as an output of the diagnostic model, the diagnostic score.

2. The computing system of claim 1, wherein the diagnostic score describes at least one of the following with respect to a patient associated with the patient audio recording:
an identity of a specific health disorder from a potential set of health disorders;
a likelihood of the patient having the specific health disorder;
a predicted severity of at least one of the specific health disorder or a health symptom; or
an estimated urgency of a need for medical attention.

3. The computing system of claim 1, wherein the diagnostic score describes a predicted severity of amyotrophic lateral sclerosis.

4. The computing system of claim 3, wherein the diagnostic score comprises a predicted functional rating scale score.

5. The computing system of claim 1, wherein the operations further comprise:
generating at least one spectrogram that describes frequency content of the patient audio recording; and
wherein the computing system inputs the spectrograms into at least one of the sound model or the diagnostic model.

6. The computing system of claim 1, wherein:
the patient audio recording comprises an audio recording of the patient uttering a predetermined text string;
the sound model is configured to recognize word sounds in the patient audio recording.

7. The computing system of claim 1, wherein:
the sound model is configured to identify sounds within two or more of a set of segments of the audio recording; and
the diagnostic model is further configured to generate a set of scores associated with the set of segments and calculate the diagnostic score based on a combination of two or more of the scores.

8. The computing system of claim 1, wherein the operations further comprise removing at least one silent or quiet portion of the patient audio recording.

9. A computer-implemented method, the method comprising:
obtaining, by one or more computing devices, a machine-learned health model that comprises a sound model and a diagnostic model, wherein the sound model is trained to receive data descriptive of a patient audio recording and, in response to receipt of the data descriptive of the patient audio recording, output sound description data, wherein the sound model comprises a machine-learned audio classification model, and wherein the sound description data comprises an embedding provided by a hidden layer of the machine-learned audio classification model, and wherein the diagnostic model is trained to receive the sound description data, and in response to receipt of the sound description data, output a diagnostic score;
inputting, by the one or more computing devices, data descriptive of the patient audio recording into the sound model;
receiving, by the one or more computing devices, as an output of the sound model, the sound description data;
inputting, by the one or more computing devices, the sound description data into the diagnostic model; and
receiving, by the one or more computing devices, the diagnostic score as an output of the diagnostic model.

10. The method of claim 9, further comprising:
generating at least one spectrogram that describes frequency content; and
inputting the spectrograms into at least one of the sound model or diagnostic model.

11. The method of claim 9, further comprising dividing the patient audio recording into a set of segments, and wherein the sound model is configured to identify sounds within two or more segments.

12. The method of claim 11, further comprising:
generating a set of segment scores associated with the set of segments; and
calculating the diagnostic score based on a combination of two or more scores of the set of scores.

13. The method of claim 9, further comprising removing at least one silent or quiet portion of the patient audio recording.

14. A computing system, comprising:
at least one processor;
a machine-learned health model comprising a diagnostic model, wherein the diagnostic model is trained to receive feature data that describes a patient audio recording, and in response to receipt of the feature data that describes the patient audio recording, output a diagnostic score; and
at least one tangible, non-transitory computer-readable medium that stores instructions that, when executed by the at least one processor, causes the at least one processor to perform operations, the operations comprising:
obtaining the patient audio recording;
generating the feature data that describes the patient audio recording, wherein the feature data comprises sound description data and generating the feature data comprises using a machine-learned sound model to generate the sound description data based on the patient audio recording, wherein the machine-learned sound model comprises a machine-learned sound classification model and wherein the sound description data comprise sound classification labels applied to the patient audio recording by the machine-learned sound classification model;
inputting the feature data that describes the patient audio recording into the diagnostic model; and
receiving, as an output of the diagnostic model, the diagnostic score.

15. A computer program which, when executed by one or more computers, causes the one or more computers to perform a method according to claim 9.

* * * * *